US00PP35306P2

(12) United States Plant Patent
Moon

(10) Patent No.: US PP35,306 P2
(45) Date of Patent: Aug. 8, 2023

(54) ***CRYPTOMERIA* TREE NAMED 'CJMTFZ'**

(50) Latin Name: *Cryptomeria japonica*
Varietal Denomination: CJMTFZ

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/903,641

(22) Filed: Sep. 6, 2022

(51) Int. Cl.
*A01H 7/00* (2006.01)

(52) U.S. Cl.
USPC ..... Plt./213

(58) Field of Classification Search
USPC ..... Plt./213
CPC ..... A01H 7/00
See application file for complete search history.

(56) References Cited

PUBLICATIONS

Oriental Garden Supply LLC for *Cryptomeria japonica* 'Dense Jade', retrieved on Dec. 6, 2022 at https://www.orientalgardensupply.com/cryptomeria-japonica-dense-jade-41468.html, 2 pp. (Year: 2022).*
Missouri Botanical Garden for *Cryptomeria japonica* 'Radicans' retrieved on Mar. 14, 2023 at https://www.missouribotanicalgarden.org/PlantFinder/PlantFinderDetails.aspx?taxonid=293811, 2 pp. (Year: 2023).*

* cited by examiner

*Primary Examiner* — June Hwu
(74) *Attorney, Agent, or Firm* — Cassandra Bright

(57) ABSTRACT

A new and distinct *Cryptomeria japonica* tree named 'CJMTFZ' is disclosed, characterized by small foliage having a thick foliar cuticle. Trees are observed to tolerate both heat and drought. The interior of the trees does not suffer from browning of the foliage, resulting in a denser, more attractive tree. A fast growth rate has been observed. The new variety is a *Cryptomeria* tree, typically used for landscapes and gardens.

3 Drawing Sheets

Latin name of the genus and species: *Cryptomeria japonica.*

Variety denomination: 'CJMTFZ'.

BACKGROUND OF THE INVENTION

The new cultivar is a product of chance discovery. The new variety was discovered growing as a whole plant mutation growing in a field of unpatented *Cryptomeria japonica* 'Yoshino' trees at a tree farm in Washington, Ga. The inventor made this discovery in 2015.

Asexual reproduction of the new cultivar 'CJMTFZ' was first performed during winter of 2016 at a farm in Washington, Ga. The process involved taking cuttings in March, placed under intermittent mist system with heat for 2 months. They are then moved into 3"×6" tree band pots and placed in greenhouses for approximately four weeks. Furthermore, these observations have confirmed that the new variety represents a new and improved variety of *Cryptomeria japonica* tree as particularly evidenced by the fastigiate growth habit. These genetic traits can be consistently reproduced by asexual propagation.

SUMMARY OF THE INVENTION

The cultivar 'CJMTFZ' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'CJMTFZ' grown in Washington, Ga. These characteristics in combination distinguish 'CJMTFZ' as a new and distinct *Cryptomeria japonica* cultivar:

1. Thick foliar cuticle.
2. Small foliage.
3. Heat and drought tolerance.
4. Dense form due to no interior browning of needles.
5. Holds up well to insect and disease pressure.
6. Fast growth rate.

PARENT COMPARISON

Plants of the new cultivar 'CJMTFZ' are similar to plants of the parent *Cryptomeria japonica* 'Yoshino' in most horticultural characteristics, however, plants of the new cultivar 'CJMTFZ' differ in the following:

1. The new variety has smaller foliage than 'Yoshino'.
2. The new variety has better heat and drought tolerance than 'Yoshino'.
3. The new variety has a denser habit because of no interior browning of needles as found with 'Yoshino'.
4. The new variety has holds up better to insects and disease than 'Yoshino'.

COMMERCIAL COMPARISON

Plants of the new cultivar 'CJMTFZ' are similar to plants of *Cryptomeria japonica* 'Atawhai', unpatented, in most horticultural characteristics, however, plants of the new cultivar 'CJMTFZ' differ in the following:

1. The new variety grows in a dense, narrow pyramidal shape, this comparator, grows in a loose, pyramidal shape.
2. Foliage of the new variety is lighter green and arranged in a more regular pattern than this comparator.

Plants of the new cultivar 'CJMTFZ' are similar to plants of *Cryptomeria japonica* 'Barabit's Gold', unpatented, in most horticultural characteristics, however, plants of the new cultivar 'CJMTFZ' differ in the following:

1. The new variety has Medium yellow-green new growth; this comparator has creamy yellow new growth.
2. The new variety grows faster than this comparator.

Plants of the new cultivar 'CJMTFZ' are similar to plants of *Cryptomeria japonica* 'Ben Franklin', unpatented, in most horticultural characteristics, however, plants of the new cultivar 'CJMTFZ' differ in the following:

1. The new variety has medium green needles; this comparator has dark green needles.
2. The new variety has a denser plant form than 'Benjamin Franklin'.

Plants of the new cultivar 'CJMTFZ' are similar to plants of *Cryptomeria japonica* 'Black Dragon', unpatented, in most horticultural characteristics, however, plants of the new cultivar 'CJMTFZ' differ in the following:

1. The new variety is not as compact in form as this comparator.
2. The new variety has medium green needles; this comparator has very dark green needles.
3. The new variety has a dense narrow pyramidal form, this comparator has a broad, irregular pyramidal form.

Plants of the new cultivar 'CJMTFZ' are similar to plants of *Cryptomeria japonica* 'Chapel View', unpatented, in most horticultural characteristics, however, plants of the new cultivar 'CJMTFZ' differ in the following:

1. The new variety has medium green colored needles; this comparator has blue-green needles.
2. Trees of 'Chapel Hill' are dwarf, trees of 'CJMTFZ' are not dwarf.
3. The new variety has a narrow pyramidal form; 'Chapel Hill' has a rounded form.

Plants of the new cultivar 'CJMTFZ' are similar to plants of *Cryptomeria japonica* 'Compacta', unpatented, in most horticultural characteristics, however, plants of the new cultivar 'CJMTFZ' differ in the following:

1. The new variety is not as compact as this comparator which grows into a narrow conical tree to 45" high.
2. The new variety has medium green needles; this comparator has bluish-green needles.

Plants of the new cultivar 'CJMTFZ' are similar to plants of *Cryptomeria japonica* 'Compressa', unpatented, in most horticultural characteristics, however, plants of the new cultivar 'CJMTFZ' differ in the following:

1. The new variety has a narrow pyramidal shape; this comparator is barrel shaped, with a bluntly rounded top.
2. The new variety has medium green needles; this comparator has dark green needles.

Plants of the new cultivar 'CJMTFZ' are similar to plants of *Cryptomeria japonica* 'Cristata', unpatented, in most horticultural characteristics, however, plants of the new cultivar 'CJMTFZ' differ in the following:

1. The new variety has upright, fan-shaped foliar branches, this comparator has fasciated, cockscombs-like tufts of foliage irregularly interspersed throughout the plant.

Plants of the new cultivar 'CJMTFZ' are similar to plants of *Cryptomeria japonica* 'Rein's Dense Jade', unpatented, in most horticultural characteristics, however, plants of the new cultivar 'CJMTFZ' differ in the following:

1. The new variety is observed to be taller and more vigorous than 'Rein's Dense Jade'. The inventor has observed 'Rein's Dense Jade' to reach approximately 10 feet in 10 years; expected height of 'CJMTFZ' is approximately 40 feet in 10 years. The American Conifer Society notes the mature height of 'Rein's Dense Jade' is approximately 8 to 10 feet after 10 years.

Plants of the new cultivar 'CJMTFZ' are similar to plants of *Cryptomeria japonica* 'Elegans', unpatented, in most horticultural characteristics, however, plants of the new cultivar 'CJMTFZ' differ in the following:

1. Foliage of the new variety is denser than foliage of this comparator.
2. Winter foliage color of the new variety is green; foliage turns brownish red in Winter.

Plants of the new cultivar 'CJMTFZ' are similar to plants of *Cryptomeria japonica* 'Elegans Aurea', unpatented, in most horticultural characteristics, however, plants of the new cultivar 'CJMTFZ' differ in the following:

1. Summer and Winter foliage color of the new variety is green, foliage of this comparator is yellow-green in Summer, turning green in Winter.

Plants of the new cultivar 'CJMTFZ' are similar to plants of *Cryptomeria japonica* 'Elegans Nana', unpatented, in most horticultural characteristics, however, plants of the new cultivar 'CJMTFZ' differ in the following:

1. Trees of 'Elegans Nana' are Flattened, globose, compact, and slow-growing; trees of 'CJMTFZ' grow rapidly and have a narrow pyramidal form.
3. Needles of 'Elegans Nana' are bluish-green, becoming purplish-tinged in winter; foliage of 'CJMTFZ' maintains a green color in the winter.

Plants of the new cultivar 'CJMTFZ' are similar to plants of *Cryptomeria japonica* 'Giokumo', unpatented, in most horticultural characteristics, however, plants of the new cultivar 'CJMTFZ' differ in the following:

1. Trees of 'Giokumo' are dwarf and reach a mature height around 8 to 10 feet, whereas trees of the new variety are expected to reach a mature height between 40 and 60 feet.

Plants of the new cultivar 'CJMTFZ' are similar to plants of *Cryptomeria japonica* 'Radicans', unpatented, in most horticultural characteristics, however, plants of the new cultivar 'CJMTFZ' differ in the following:

1. The new variety does not have the dead, browning needles in the interior as significantly found in this comparator.

Plants of the new cultivar 'CJMTFZ' are similar to plants of *Cryptomeria japonica* 'Green Grizzly', unpatented, in most horticultural characteristics, however, plants of the new cultivar 'CJMTFZ' differ in the following:

1. The new variety forms a much denser plant than this comparator.

Plants of the new cultivar 'CJMTFZ' are similar to plants of *Cryptomeria japonica* 'Gyokuryu', unpatented, in most horticultural characteristics, however, plants of the new cultivar 'CJMTFZ' differ in the following:

1. The new variety has a much narrower plant form than this comparator.

Plants of the new cultivar 'CJMTFZ' are similar to plants of *Cryptomeria japonica* 'Jindai', unpatented, in most horticultural characteristics, however, plants of the new cultivar 'CJMTFZ' differ in the following:

1. The new variety has a much narrower plant form than this comparator.
2. The new variety grows more rapidly than this comparator.

Plants of the new cultivar 'CJMTFZ' are similar to plants of *Cryptomeria japonica* 'Kilmacurragh', unpatented, in most horticultural characteristics, however, plants of the new cultivar 'CJMTFZ' differ in the following:

1. The new variety is a tall, narrow pyramidal tree with fan-shaped foliar branches, this comparator is a low-growing form with small foliage fasciations.

Plants of the new cultivar 'CJMTFZ' are similar to plants of *Cryptomeria japonica* 'Knaptonensis', unpatented, in most horticultural characteristics, however, plants of the new cultivar 'CJMTFZ' differ in the following:

1. New growth of the new variety is yellow-green; new growth of this comparator is creamy white.

Plants of the new cultivar 'CJMTFZ' are similar to plants of *Cryptomeria japonica* 'Lobbii', unpatented, in most horticultural characteristics, however, plants of the new cultivar 'CJMTFZ' differ in the following:

1. Plant form of the new variety is narrow pyramical; plant form of this comparator is a broader, irregular pyramid.

BRIEF DESCRIPTION OF THE PHOTOGRAPHS

The accompanying photograph in FIG. 1 illustrates a typical tree of the new variety at about 3 years of age.

Figure 1:
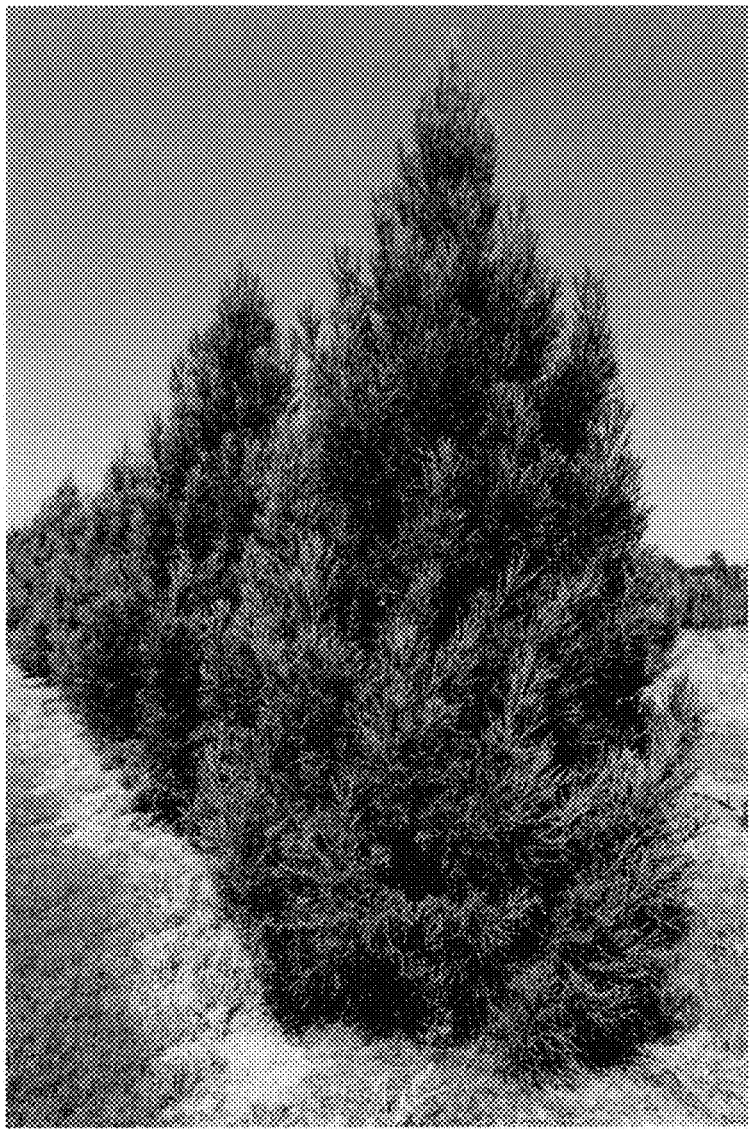
Figure 2:
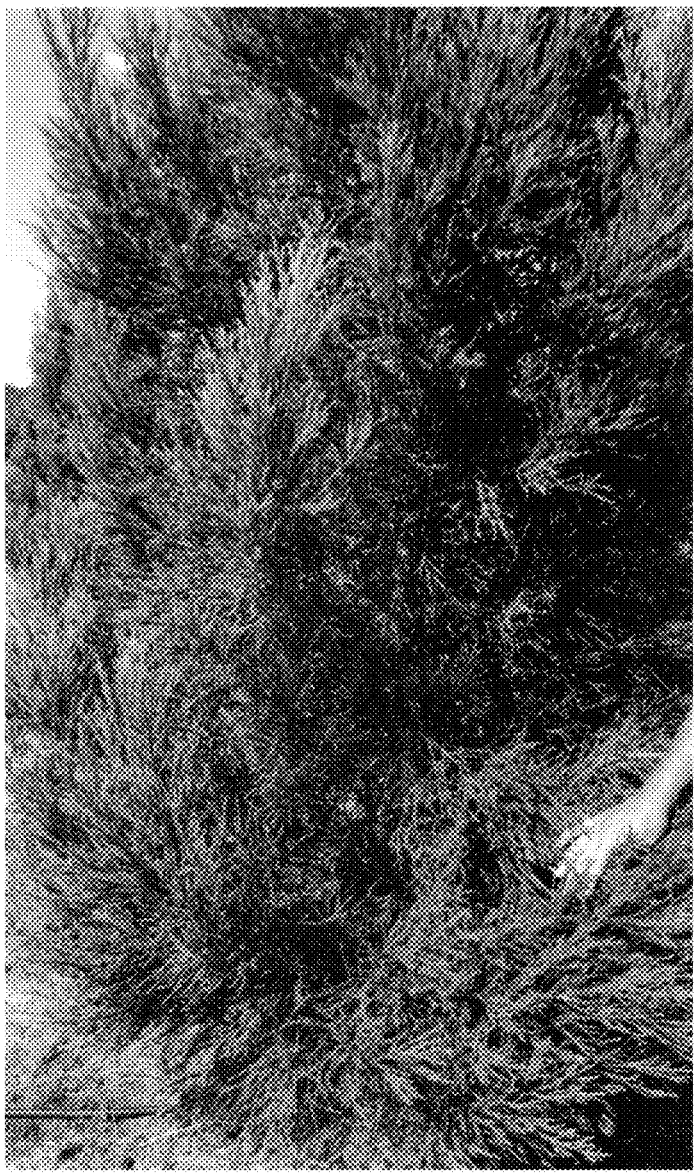
FIG. 2 illustrates the density of the growth.
Figure 3:
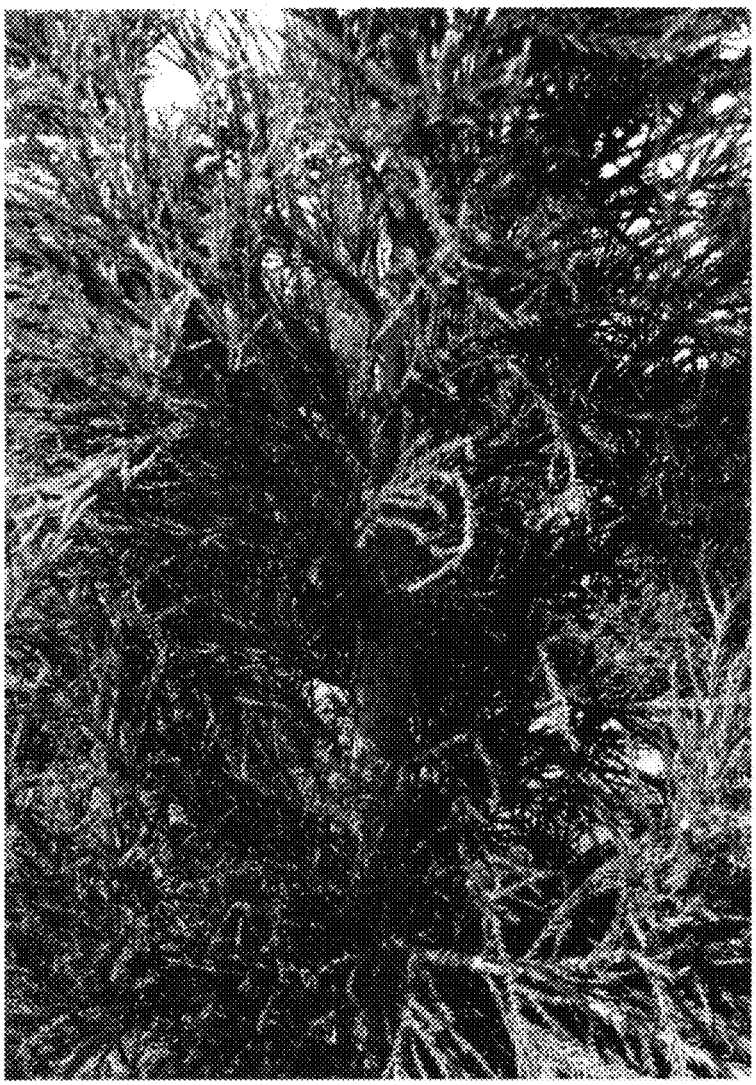
FIG. 3 illustrates a closer view of the interior of the tree.

All trees illustrated are field grown in Washington, Ga. Trees are approximately 3 years from planting into the field. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'CJMTFZ' plants grown outdoors and in a nursery in Washington, Ga. Plants are approximately 3 years old, planted in the ground. Temperatures ranged from about 2° C. to 10° C. at night to 18° C. to 39° C. during the day. Measurements and numerical values represent averages of typical plant types.

Botanical classification: *Cryptomeria japonica* 'CJMTFZ'.

PROPAGATION

Cuttings taken in early Spring are placed under mist at approximately 25° C. for approximately 2 months. These cuttings are then removed from mist and greenhouse grown for another approximately 4 weeks before moving outside.

Root description: Woody. Brown roots not accurately measured with an R.H.S. Colour chart.

TREE

Growth habit: Evergreen narrow pyramidal tree.
Height: Approximately 12 feet at 3 years.
Spread: Approximately 5 feet at 3 years.
Aspect and angle: Branches at acute angles, 45 degrees or less.
Growth rate: Rapid.
Branching habit: Occurring from center, upswept, acute.
Length of lateral branches: 30 cm to 60 cm.
Average number of lateral branches: 70-100.
Diameter of lateral branches: 3 cm.
Lateral branch color: Near RHS Greyed-Orange 176D flushed Brown N200D with scales near Brown N200C and N200D.
Lateral branch strength: Very strong.
Internode length: Average range 10 cm to 15 cm.
Trunk characteristics:

*Diameter*.—About 3 inches measured at approximately 3 inches above soil level at 3 years.
*Color*.—Near RHS Greyed-Orange 176D flushed Brown N200D with large scales near Brown N200C and N200D.
*Surface texture*.—Large scaly bark.

FOLIAGE

Leaf:

*Arrangement*.—Spiral.
*Shape*.—Awl-shaped.
*Average length*.—Approximately 3 to 5 mm.
*Average width*.—Approximately 2 to 3 mm.
*Apex*.—Acute.
*Base*.—Truncate.
*Margin*.—Entire.
*Texture of top surface*.—Glabrous.
*Texture of bottom surface*.—Glabrous.
*Color*.—Young foliage upper side: Near RHS Yellow-Green 144B flushed Yellow-Green N144B. Young foliage under side: Near RHS Yellow-Green 144B flushed Yellow-Green N144B. Mature foliage upper side: Near RHS Green 137C. Mature foliage under side: Near RHS Green 137C. Winter foliage upper side: Near RHS Green 137C. Winter foliage under side: Near RHS Green 137C.
*Venation*.—Indistinguishable from leaf blade.
*Fragrance*.—Cedarlike.

FLOWER

Flowering and cone production not observed.

REPRODUCTIVE ORGANS

Not observed.

OTHER CHARACTERISTICS

Disease/pest resistance: Resistance to normal diseases and pests of *Cryptomeria* has been observed. Additionally, due to the dark green foliage, the new variety exhibits resistance to mites. Resistance to leaf blight and leaf spot which causes branches to die back has been observed.

Drought tolerance: Some drought observed. *Cryptomeria japonica* can be moderately drought tolerance once established.

Temperature tolerance: Observed growing at temperatures between 10° F. to 102° F.

Fruits/nuts: Not observed.

What is claimed is:

1. A new and distinct cultivar of *Cryptomeria japonica* tree named 'CJMTFZ' as herein illustrated and described.

* * * * *